United States Patent
Mouchawar et al.

(10) Patent No.: US 6,553,259 B2
(45) Date of Patent: Apr. 22, 2003

(54) SYSTEM AND METHOD OF PERFORMING AUTOMATIC CAPTURE IN AN IMPLANTABLE CARDIAC STIMULATION DEVICE

(75) Inventors: Gabriel A. Mouchawar, Newhall, CA (US); Jorge N. Amely-Velez, Simi Valley, CA (US); George I. Isaac, Port Hueneme, CA (US); Steven W. Badelt, Granada Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 128 days.

(21) Appl. No.: 09/810,929

(22) Filed: Mar. 14, 2001

(65) Prior Publication Data

US 2002/0133203 A1 Sep. 19, 2002

(51) Int. Cl.$^7$ ............................................. A61N 1/362
(52) U.S. Cl. ............................ 607/11; 607/25; 607/28
(58) Field of Search ............................ 607/11, 17, 25, 607/28

(56) References Cited

U.S. PATENT DOCUMENTS

| | | | |
|---|---|---|---|
| 4,712,555 A | 12/1987 | Thornander et al. | 128/419 |
| 4,788,980 A | 12/1988 | Mann et al. | 128/419 |
| 4,940,052 A | 7/1990 | Mann et al. | 128/419 |
| 4,944,298 A | 7/1990 | Sholder | 128/419 |
| 5,339,820 A * | 8/1994 | Henry et al. | 600/508 |
| 5,350,401 A | 9/1994 | Levine | 607/4 |
| 5,350,410 A | 9/1994 | Kleks et al. | 607/28 |
| 5,466,254 A | 11/1995 | Helland | 607/123 |
| 5,573,550 A | 11/1996 | Zadeh et al. | 607/28 |
| 5,685,315 A | 11/1997 | McClure et al. | 128/708 |
| 5,713,934 A * | 2/1998 | Leckrone | 607/28 |
| 5,843,136 A | 12/1998 | Zhu et al. | 607/13 |
| 6,016,446 A | 1/2000 | Belalcazar | 607/13 |
| 6,044,296 A | 3/2000 | Zhu et al. | 607/13 |
| 6,430,441 B1 * | 8/2002 | Levine | 607/28 |

* cited by examiner

*Primary Examiner*—Andrew M. Dolinar

(57) ABSTRACT

An implantable cardiac stimulation device possessing pacing, cardioversion and defibrillation functions and automatic capture capabilities, for automatically verifying capture during stimulation operations and, as necessary, automatically delivering back-up stimulation pulses when capture is lost, and subsequently adjusting the stimulation energy to a level safely above that needed to achieve capture. The stimulation device utilizes a method for maintaining capture by means of a capture search algorithm, so that whenever loss of capture is detected, it re-determines the minimum stimulation energy required to achieve capture. Another aspect of the stimulation device is the automatic threshold testing which is invoked to determine the minimum stimulation pulse energy needed to ensure capture. When the automatic capture function is enabled, the stimulation device initiates a stimulation refractory period, upon the expiration of which, the stimulation device sets a sensing threshold to a predetermined level and then either maintaining this level fixed or causing it to decay, during an alert interval. Concurrently, the stimulation device verifies capture during the alert interval.

38 Claims, 10 Drawing Sheets

SYSTEM AND METHOD OF PERFORMING AUTOMATIC CAPTURE IN AN IMPLANTABLE CARDIAC STIMULATION DEVICE

FIELD OF THE INVENTION

The present invention relates to an implantable cardiac stimulation device capable of delivering both high and low voltage therapies for treating bradycardia, tachycardia, and fibrillation. The present invention relates more specifically to an implantable cardiac stimulation device possessing automatic sensitivity control and beat-by-beat automatic capture.

BACKGROUND OF THE INVENTION

Implantable cardiac stimulating devices include pacemakers and cardioverter defibrillators (ICDs). A primary function of pacemakers is to detect and treat incidents of a slow heart rate, known as bradycardia, or no heart rate, known as asystole. A primary function of ICDs is to detect and treat incidents of an excessively high heart rate, known as tachycardia, or incidents of fibrillation.

Combined pacemaker/cardioverter defibrillators are commercially available for treating both bradycardia, and tachycardia or fibrillation. Such a combined cardiac stimulating device is coupled to the patient's heart through transvenous leads which are used to sense electrical signals from the heart, and deliver both low voltage and high voltage electrical therapy to the heart.

The pacemaker circuitry generally includes sensing circuitry for sensing cardiac electrical activities in order to detect intrinsic electrical depolarizations of the cardiac tissue that cause contraction of the respective heart chambers. In the atria, detection of a P-wave indicates atrial contraction, and in the ventricles detection of an R-wave, also known as a QRS complex, indicates ventricular contraction.

If detection of an intrinsic P-wave or an R-wave does not occur within a given interval of time, generally referred to as the "escape interval," the heart rate is determined as being too slow. A stimulation pulse is then generated by the pacemaker circuitry and delivered to the appropriate heart chamber at the end of the escape interval in order to stimulate the muscle tissue of the heart to contract, thus maintaining a minimum heart rate. The duration of the escape interval corresponds to some base pacing rate, for example an escape interval of 1,200 msec would maintain a base pacing rate of 50 heart beats per minute.

The electrical depolarization caused by delivery of a pacing pulse is known as an "evoked response." An evoked response occurs when the stimulating pulse is of sufficient energy to cause depolarization of the cardiac tissue, a condition known as "capture." The minimum stimulating energy required to capture a chamber of the heart is known as "threshold."

Modern pacemakers often include a feature known as "automatic capture." When automatic capture is implemented, the pacemaker circuitry detects the evoked response following delivery of a pacing pulse in order to verify that capture has occurred. If no evoked response is detected, the pacing pulse may have been of insufficient energy to capture the heart; therefore, a high-energy back-up pacing pulse is quickly delivered to the heart in order to maintain the desired heart rate. A threshold detection algorithm is next invoked in order to re-determine what minimum energy is required to capture the heart. The pacing pulse energy is then automatically adjusted to this new threshold value plus some safety margin. As long as an evoked response is detected following a pacing pulse, that is as long as capture is verified, pacing will continue at the set rate and pulse energy. Hence automatic capture improves pacemaker performance in at least two ways: 1) it verifies that the stimulation therapy delivered has been effective in pacing the heart chamber, and 2) it improves battery energy longevity by determining the lowest stimulation energy needed to effectively capture the heart.

The cardioverter defibrillator circuitry of an implantable cardiac stimulating device monitors the electrical activity of the heart to detect when the intrinsic heart rate exceeds a defined upper rate limit. In the case of tachycardia, a high energy stimulation pulse is usually delivered in synchrony with the heart's QRS wave in an attempt to terminate the tachycardia, a treatment known as "cardioversion." Synchronized delivery of the high-energy pulse prevents stimulating the heart during the T-wave portion of the P-QRS-T cardiac cycle. During the T-wave portion of the cardiac cycle, the ventricular tissue is re-polarizing and delivery of any kind of stimulation pulse during this time could accelerate the heart rhythm into a faster tachycardia or even into fibrillation.

A serious form of tachycardia is ventricular fibrillation, which is usually fatal if not treated within a few minutes of occurrence. During fibrillation, disorganized depolarizations occur throughout the heart tissue (myocardium) causing the heart chamber to contract in a chaotic way, i.e., fibrillate, resulting in ineffective ejection of blood from the heart chamber. These disorganized depolarizations, also referred to as fibrillation waves, are typically low amplitude signals that occur at an irregular rate. When the cardioverter-defibrillator circuitry detects fibrillation, a high energy shocking pulse is delivered in an attempt to re-coordinate the depolarization of all (or most of) the individual muscle fibers and thus regain coordinated cardiac contractions.

In order to allow detection of both higher amplitude R-waves and low amplitude fibrillation signals, implantable cardioverter defibrillators commonly include automatic gain control or automatic sensitivity control for detecting both high amplitude R-waves and low-amplitude fibrillation signals. Reference is made to U.S. Pat. No. 5,685,315 to McClure et at. for a more detailed description of the use of automatic sensitivity control in cardiac arrhythmia detection, herein incorporated by reference. Automatic gain or sensitivity control allows straightforward detection of cardiac events based on event amplitude crossing of the sensing threshold. An initially higher sensing threshold is applied starting at the end of a refractory period that follows a detected P-wave or R-wave or a delivered pacing pulse. As the gain or sensitivity decays, detection of low amplitude fibrillation waves is possible. The rate at which the detected events occur allows classification of the detected rhythm into bradycardia, normal sinus, low rate tachycardia, high rate tachycardia, or fibrillation.

However, a problem exists for patients having a combined pacemaker cardioverter defibrillator in that the electrogram signal from the ventricular fibrillation may be so low in amplitude that neither the ICD nor the pacemaker sensing circuits sense anything, thus causing the pacemaker portion of the system to release a stimulation pulse. Upon releasing the stimulus, the automatic sensitivity feature the sensing circuits of the stimulation device, if enabled, incrementally increases its sensitivity to its most sensitive setting, in an attempt to sense an R-wave. If a failure to sense an R-wave persists, the diagnosis is "true asystole," and the stimulation device will continue to release stimulation pulses at its programmed base pacing rate. However, if the rhythm is truly ventricular fibrillation with an electromyogram signal that is too low to be sensed by either the stimulation device, the stimulation pulses will not be effective. However, the stimulation device does not recognize the ineffectiveness of the stimulation pulses, and will continue to deliver such ineffective stimuli.

Therefore, what is needed is a combined stimulation device or system wherein a proper response to an alleged asystole can occur, and wherein the device can ascertain whether or not a given stimulation pulse is effective, i.e., whether it "captures" the heart. The automatic capture feature is therefore also desirable in a combined ICD/pacemaker in order to ensure effective stimulation therapy and to increase device longevity by conserving battery energy. The importance of providing automatic capture is described in U.S. Pat. No. 5,350,401, to Levine, which is incorporated herein by reference.

One problem in determining capture is the phenomenon known as "lead polarization." Lead polarization is commonly caused by electrochemical reactions that occur at the electrode-tissue interface following delivery of an electrical stimulation pulse. However, the polarization signal, also referred to as an "afterpotential," can corrupt the evoked response signal that is sensed by the sensing circuits. This undesirable situation occurs because the polarization signal can be three or more orders of magnitude greater than the evoked response. Furthermore, the polarization signal is not easily characterized; it is a complex function of the lead materials, lead geometry, tissue impedance, stimulation energy and other variables, many of which are continually changing over time.

One way to minimize the effect of lead polarization in pacemakers is to sense through a different combination of electrodes than the electrodes used for delivery of stimulation pulses. For example, it is possible to stimulate in a unipolar configuration, using the tip electrode of a bipolar lead as the cathode and the device housing as the anode, and to sense the heart signals in a bipolar configuration using the ring electrode and tip electrode of the same bipolar lead. By using a different electrode combination for sensing than for pacing, saturation of the sensing amplifier due to lead polarization is avoided. However, in combined ICD/pacemaker systems, electrode configuration switching from unipolar pacing to bipolar sensing, or various other configurations, is generally not available for the reason that unipolar pacing in cardioverter defibrillators is not desirable because it may interfere with arrhythmia detection. Pacing stimulation is generally delivered in a bipolar configuration via a tip electrode and a ring and/or coil electrode, the same electrodes that may be used for sensing.

Other methods of reducing lead polarization effects are known such as emitting a pulse of the opposite polarity (discharge pulse) immediately after the stimulation pulse. However, minimizing lead polarization effects alone, does not completely solve the problem of evoked response detection in cardiac stimulation devices combining pacemaking, cardioversion and defibrillation functions.

A refractory period is typically applied immediately following a pacing pulse or a detected intrinsic depolarization. The refractory period primarily prevents the sensing of T-waves, which follow the QRS complex. Over-sensing of T-waves could cause inappropriate tachycardia detection resulting in unnecessary, potentially harmful, therapy delivery. The refractory period is kept as short as possible in order to maximize the window for sensing high rate rhythms, but must be long enough to prevent over-sensing of T-waves. This refractory period therefore, could prevent detection of the evoked response following a pacing pulse.

One way of discriminating between T-waves and R-waves would be to use digitized EGM signals for comparison to depolarization signal templates. For example, a method for automatic capture in an implantable pulse generator can allow for comparison between an EMG signal and a depolarization template after analog-to-digital conversion of these signals. Reference is made to U.S. Pat. No. 5,350,410 to Kleks et al. However, many implantable defibrillators include digitized electrogram storage so that cardiac electrical activity leading up to an arrhythmic episode may be analyzed. Digitized EGM signals are stored in memory and later recalled in order to provide useful diagnostic information. Hence, the microprocessor of the ICD/pacemaker device may be busy collecting and digitizing EGM signals from sources other than the chamber in which a pacing pulse was delivered, making the EGM analog-to-digital converter unavailable for capture verification. Digitized EGM signal detection dedicated to capture verification on a beat-by-beat basis during pacing would require precious microprocessor time and, without additional circuitry, would likely be provided at the cost of disregarding EGM data collection and storage in a combined ICD/pacemaker.

It would thus be desirable to provide an implantable cardiac stimulating device possessing pacing, cardioversion, and defibrillation functions in which capture verification can be performed. Further, it would be desirable to provide beat-by-beat capture verification during pacing operations without additional hardware or circuitry and without extensive consumption of microprocessor time. It would also be desirable to provide a system capable of automatically searching for the capture threshold whenever capture is lost and appropriately adjusting the pacing energy to the new threshold level plus some safety margin, thus providing the advantages of automatic capture in a combined ICD/pacemaker device without introducing any known disadvantages.

SUMMARY OF THE INVENTION

The present invention addresses the foregoing problems by providing an implantable cardiac stimulation device possessing pacing, cardioversion and defibrillation functions and automatic capture capabilities, for automatically verifying capture during stimulation operations and, as necessary, automatically delivering back-up stimulation pulses when capture is lost, and subsequently adjusting the stimulation energy to a level safely above that needed to achieve capture.

One aspect of the present invention is a method for detecting the presence or absence of an evoked response following the delivery of a stimulation pulse. This capture verification method advantageously utilizes the automatic sensitivity control hardware commonly included in implanted cardioverter defibrillator systems to allow a straight-forward threshold detection technique, thus avoiding more intensive signal recognition schemes. In the case of no evoked response detection, the circuitry of the stimulation device is notified of the capture failure and is enabled to provide a back-up stimulation pulse in order to sustain the desired contraction rate.

A further aspect of the present invention includes a method for maintaining capture by using a capture search algorithm. Whenever loss of capture is detected, the minimum stimulation energy required to achieve capture is re-determined by delivering test stimulation pulses at progressively increasing or decreasing energy levels, using the capture verification method of the present invention to detect when capture is achieved or lost. In so doing, battery longevity of the cardiac stimulating device is improved by maintaining the lowest energy needed to deliver effective stimulation therapy.

Another aspect of the present invention includes automatic threshold testing that can be invoked on an event-triggered or periodic basis in order to determine the minimum stimulation pulse energy needed to ensure capture. Such a threshold test is implemented in a cardiac stimulation device possessing a method for verifying capture. Using the capture verification method of the present invention, automatic threshold testing in a combined ICD/pacemaker stimulation device is provided.

One embodiment of the present invention is, therefore, an implantable cardiac stimulation device including a method for sensing cardiac events and delivering both high and low voltage stimulation therapies for appropriately treating bradycardia, tachycardia, or fibrillation. One method of therapy delivery includes: 1) sensing for cardiac activity within a cardiac chamber during a defined escape interval; 2) when intrinsic cardiac activity is not detected within the given escape interval, delivering a stimulation pulse for the purpose of stimulating the cardiac chamber to contract at a desired rate; 3) verifying that the delivered stimulation pulse produced an evoked response by sensing during an alert interval following a short refractory period; 4) if no evoked response is detected during the alert interval, sustaining the desired stimulation rate by delivering a back-up stimulation pulse; 5) whenever a back-up stimulation pulse is required, performing a capture search for determining the minimum pulse energy needed to reliably achieve capture, and 6) adjusting the programmed stimulation energy to a level safely above the newly determined capture energy. When the automatic capture function is enabled, the stimulation device initiates a stimulation refractory period, upon the expiration of which, the stimulation device sets a sensing threshold to an evoked response threshold. During the alert interval, the evoked response threshold could be constant or decaying. Concurrently, the stimulation device verifies capture during the alert interval.

Thus, one feature of the present invention is a method for automatically and reliably ensuring that capture occurs during stimulation operations of an implantable ICD/pacemaker (also referred to herein as stimulation device). Another feature of the present invention is to provide reliable threshold testing in an implantable cardiac stimulation device. By providing automatic capture and automatic threshold testing, the stimulation device performance and battery longevity are improved.

BRIEF DESCRIPTION OF THE DRAWINGS

Further features and advantages of the present invention may be more readily understood by reference to the following description taken in conjunction with the accompanying drawings, in which:

FIG. 5 is comprised of FIGS. 6 and 7, illustrating a flow chart that describes an overview of one embodiment of a capture verification mode included in the automatic capture feature of FIG. 5 when an evoked response is not detected following delivery of a stimulation pulse;

DETAILED DESCRIPTION OF THE INVENTION

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout. The present invention is directed at providing automatic capture in an implantable cardiac stimulating device possessing pacemaking, cardioversion and defibrillation capabilities. A general cardiac stimulation device will thus be described in conjunction with FIGS. 1 and 2, in which the automatic capture feature of the present invention could be implemented. It is recognized, however, that numerous variations of such a device exist in which the methods of the present invention could be implemented without deviating from the scope of the present invention.

Figure 1:
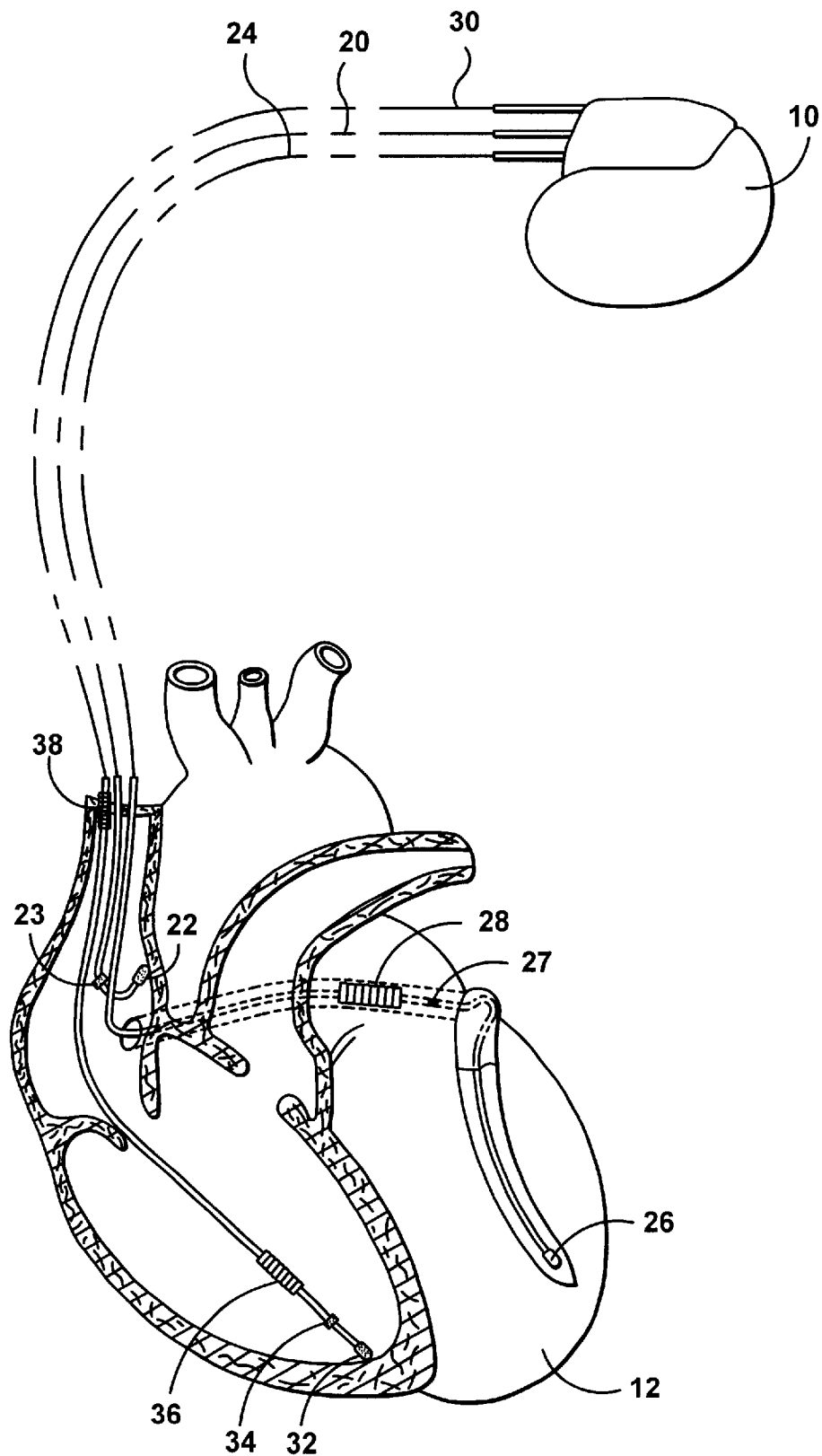
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a more detailed description of a coronary sinus lead, refer to U.S. patent application Ser. No. 09/196,898, titled "A Self-Anchoring Coronary Sinus Lead" (Pianca et. al), and U.S. Pat. No. 5,466,254, titled "Coronary Sinus Lead with Atrial Sensing Capability" (Helland), herein incorporated by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
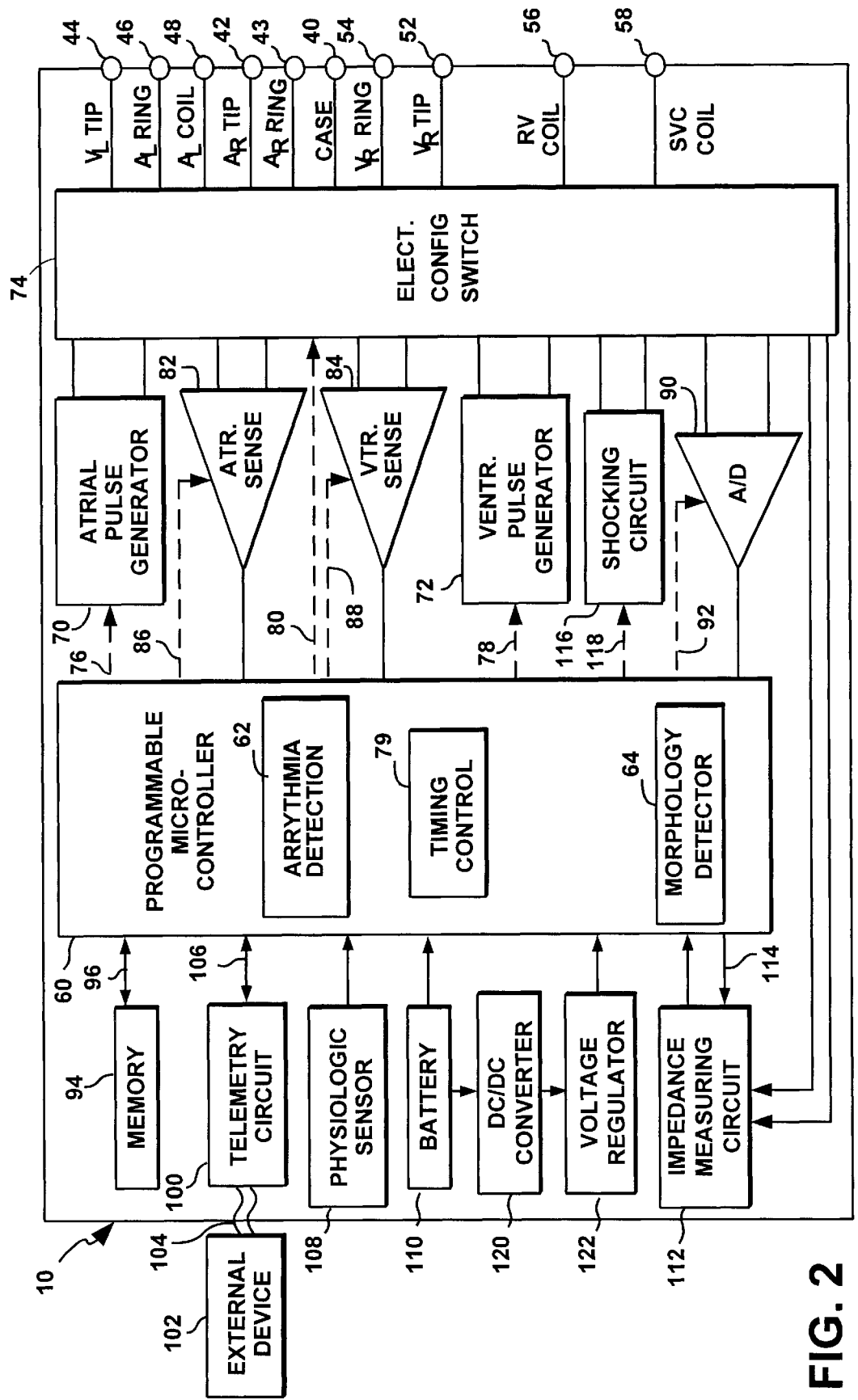
FIG. 2 is a functional block diagram of the multi-chamber implantable stimulation device of FIG. 1, illustrating the basic elements that provide cardioversion, defibrillation and pacing stimulation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector having a plurality of terminals 42, 43, 44, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal 42 adapted for connection to the atrial ($A_R$) tip electrode 22. The connector may also include a right atrial ring terminal 43 for connection to the atrial ($A_R$) ring electrode 23.

To achieve left chamber sensing, pacing, and shocking, the connector includes at least a left ventricular ($V_L$) tip terminal 44, a left atrial ($A_L$) ring terminal 46, and a left atrial ($A_L$) shocking coil terminal 48, which are adapted for connection to the left ventricular tip electrode 26, the left atrial ring electrode 27, and the left atrial coil electrode 28, respectively.

To support right ventricular sensing, pacing and shocking, the connector further includes a right ventricular ($V_R$) tip terminal 52, a right ventricular ($V_R$) ring terminal 54, a right ventricular (RV) shocking coil terminal 56, and an SVC shocking coil terminal 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Representative types of control circuitry that may be used with the present invention include the microprocessor-based control system of U.S. Pat. No. 4,940,052 (Mann et. al), which is incorporated herein by reference. For a more detailed description of the various timing intervals used within the stimulation device and their inter-relationship, reference is made to U.S. Pat. No. 4,788,980 (Mann et. al), incorporated herein by reference.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A—A) delay, or ventricular interconduction (V—V) delay, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, combipolar, etc.) by selectively closing the appropriate combination of switches (not shown) as is known in the art. Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

Stimulation during pacing can be performed in a bipolar mode in devices combining pacing and cardioversion/defibrillation functions because unipolar stimulation may interfere with arrhythmia detection. Hence, in one embodiment of the present invention, the switch bank 74 is configured such that right atrial pacing and sensing is performed in a bipolar fashion between the right atrial tip electrode 22 and right atrial ring electrode 23; right ventricular pacing and sensing is performed in a bipolar fashion between right ventricular tip electrode 32 and right ventricular ring electrode 34; and left ventricular pacing and sensing is performed in a bipolar fashion between coronary sinus tip electrode 26 and the coronary sinus ring electrode 27. Right ventricular sensing may alternatively be configured between the right ventricular coil electrode 36 and the right ventricular ring electrode 34. Bipolar sensing may also be achieved using an integrated bipolar lead wherein the right ventricular coil electrode 36 and right ventricular ring electrode 34 are electrically coupled within the right ventricular lead body 30. Bipolar sensing is then performed between the right ventricular tip electrode 32 and the coupled right ventricular coil electrode 36 and right ventricular ring electrode 34. The electrode combinations used for pacing and sensing are not critical to the present invention. Rather, any electrode combination that allows acceptable stimulation and sensing thresholds may be used. By employing the right ventricular coil electrode 36, possibly in combination with right ventricular ring electrode 34, the electrode surface during sensing is increased, advantageously reducing the effects of lead polarization. Other techniques of reducing lead polarization such as titanium nitride coating may also be used to improve the operation of the present invention.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation. For a more detailed description of a sensing circuit, reference is made to U.S. Pat. No. 5,573,550, titled "Implantable Stimulation Device having a Low Noise, Low Power, Precision Amplifier for Amplifying Cardiac Signals" (Zadeh et al.), incorporated herein by reference. For a more detailed description of an automatic sensitivity control system, reference is made to U.S. Pat. No. 5,685,315, titled "Cardiac Arrhythmia Detection System for an Implantable Stimulation Device" (McClure et al), incorporated herein by reference.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.), in order to determine the type of remedial therapy that is needed (e.g. bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". As it will be described in detail in conjunction with FIGS. 5 through 13, when the automatic capture feature of the present invention is enabled, the microcontroller 60 detects a depolarization signal during an "alert interval" following a stimulation pulse. The presence of an evoked response indicates that capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various stimulation parameters (such as rate, AV Delay, V—V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 $\mu$A, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected. Accordingly, the stimulation device 10 can employ lithium/silver vanadium oxide batteries.

In order to provide high energy stimulation pulses in accordance with the present invention, the battery 110 is connected to a DC/DC converter 120 and linear voltage regulator 122. In a preferred embodiment, when capture does not occur at a programmed stimulation energy, the DC/DC converter 120 and linear voltage regulator 122 are employed in charging an output capacitor included in atrial and/or ventricular pulse generator circuitry 70 and/or 72 for delivering a backup stimulation pulse amplitude greater than the battery voltage, for example twice the battery voltage. During stimulation delivery at lower level energies, the DC/DC converter 120 and linear voltage regulator 122 can be bypassed allowing the stimulating pulse energy to be derived exclusively from the battery 110, thus minimizing power consumption.

As further illustrated in FIG. 2, the stimulation device 10 is shown to include an impedance measuring circuit 112 which is enabled by the microcontroller 60 by means of a control signal 114.

It is a primary function of the stimulation device 10 to operate as an implantable cardioverter/defibrillator (ICD) device. That is, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
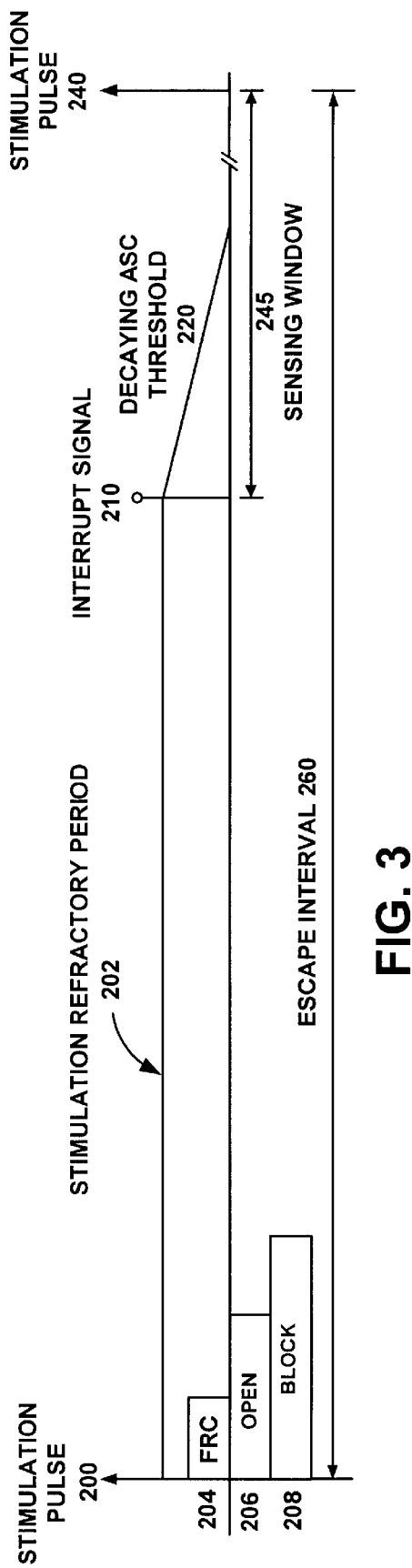
FIG. 3 is a timing diagram illustrating a sequence of events that occur during one escape interval when the automatic capture feature of the present invention is not enabled in the implantable stimulation device of FIG. 2.

In FIG. 3, a timing diagram illustrates a sequence of operations carried out by the stimulation device 10 under the control of the microprocessor 60 when the automatic capture feature of the present invention is not enabled. Immediately following the delivery of a stimulation pulse 200, a stimulation refractory period 202 is initiated. The duration of the stimulation refractory period 202 is preferably programmable. For illustration purpose only, the stimulation refractory period 202 is programmed to a duration of approximately 256 msec. The purpose of the stimulation refractory period is normally to prevent inappropriate tachycardia detection by preventing the atrial sensing circuitry 82 or the ventricular sensing circuitry 84 (FIG. 2) from sensing events associated with the evoked response that normally follow the stimulation pulse, for example T-waves. If these events are detected, the arrhythmia detection circuitry of the stimulation device 10 may inappropriately detect tachycardia and deliver inappropriate anti-tachycardia therapies.

During the stimulation refractory period 202, three sequential events take place. First, a fast recharge period (FRC) 204 is initiated immediately following the stimulation pulse. The fast recharge interval 204 allows charge balancing to occur quickly through the heart tissue, thereby minimizing the effects of lead polarization. The fast recharge interval 204 is also a programmable value and is programmed, for example, to approximately 15 msec. Immediately following the fast recharge interval 204, an OPEN interval 206 and BLOCK interval 208 are sequentially initiated. The OPEN interval 206 and BLOCK interval 208 are initiated and terminated by the opening and closing of switches located in an automatic sensitivity control (ASC) hardware within the atrial or ventricular sensing circuitry 82 or 84, respectively.

Figure 4:
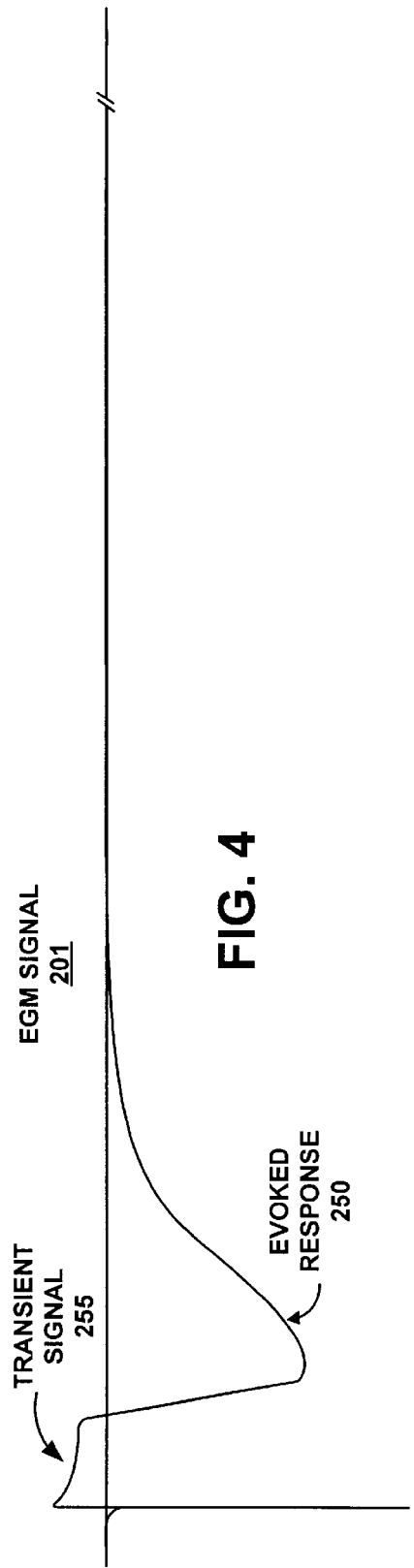
FIG. 4 is a trace representing an EGM signal corresponding to the timing diagram of FIG. 3.

The trace illustrated in FIG. 4 represents the EGM signal 201 corresponding to the timing diagram of FIG. 3. A large transient signal 255 is associated with the delivery of the stimulation pulse 200. The purpose of the OPEN interval 206 and the BLOCK interval 208 is to isolate the sense amplifier from the transient signal 255. The sense amplifier of the atrial and/or ventricular sensing circuitry 82 and/or 84, respectively, is connected to a reference potential so that the sense amplifier does not receive the large transient signal 255 and so that this transient signal 255 is not digitized by the analog-to-digital data acquisition system 90. The OPEN interval 206 and the BLOCK interval 208 are programmed, for example, to a 15 msec overlap.

The transient signal 255 is followed by a large depolarization 250 associated with the evoked response when capture occurs. As is illustrated in FIGS. 3 and 4, with the automatic capture feature of the present invention not enabled, the evoked response occurs within the stimulation refractory period 202 and therefore goes undetected. No capture verification can take place.

Upon expiration of the stimulation refractory period 202, an interrupt signal 210 is generated to the microprocessor 60 to indicate that the stimulation refractory period 202 has expired. This interrupt signal 210 is used by microprocessor 60 to trigger other system operations to take place including the initiation of sensing during the remaining time of the pre-defined escape interval corresponding to the programmed base stimulation rate.

The automatic sensitivity control (ASC) hardware of the sensing circuitry 82 or 84 initially sets the sensing threshold 220 to a high level to allow detection of higher amplitude R-waves or P-waves but not lower level signals such as T-waves. The sensing threshold 220 then decays at a rate controlled by the automatic sensitivity control (ASC) hardware. As the sensing threshold 220 decays, low amplitude signals, such as those associated with fibrillation, can be detected. If no intrinsic depolarization or fibrillation is detected during the sensing window 245, another stimulation pulse 240 will be delivered upon expiration of the escape interval 260.

The events illustrated in FIG. 3 may represent events occurring in either the atria or the ventricles. For example, the stimulation pulse 200 may represent an atrial stimulation pulse delivered by the atrial pulse generator 70 or a ventricular stimulation pulse delivered by the ventricular pulse generator 72. The next stimulation pulse 240 may then represent an atrial stimulation pulse generated by the atrial pulse generator 70 upon the expiration of an intra-atrial (AA) escape interval or expiration of a ventricular-to-atrial (VA) escape interval. The stimulation pulse 240 could also represent a ventricular stimulation pulse generated by ventricular pulse generator 72 upon the expiration of an intra-ventricular (V—V) escape interval. Hence, the events illustrated in FIG. 3 represent one complete escape interval 260 which may be a VV interval, a VVR interval (rate-responsive VV interval), a VA interval, a VAR interval (rate-responsive VA interval), and so forth.

If an R-wave or a P-wave is detected during the sensing window 245, the stimulation pulse 240 would be appropriately inhibited. If the detected R-wave or P-wave occurs at a rate exceeding the tachycardia detection rate, the stimulation device 10 will act appropriately in verifying a tachycardia or fibrillation detection and delivering cardioversion or defibrillation therapy as necessary.

However, the stimulation operations of the stimulation device 10 as illustrated in FIG. 3 are functioning in a somewhat "blinded" fashion in that no confirmation of successful capture is made following the stimulation pulse 200. If the capture threshold has increased above the output pulse parameters, the delivered stimulation pulse will have no effect. Yet, if no intrinsic response is detected during the sensing window 245, another stimulation pulse 240 will be delivered, providing no benefit to the patient as the patient could be asystolic. The events of FIG. 3 will thus continue to be repeated, resulting in ineffective stimulation therapy during a potentially life-threatening situation for the patient. To alleviate this potential problem, the automatic capture feature of the present invention may be employed.

Figure 5:
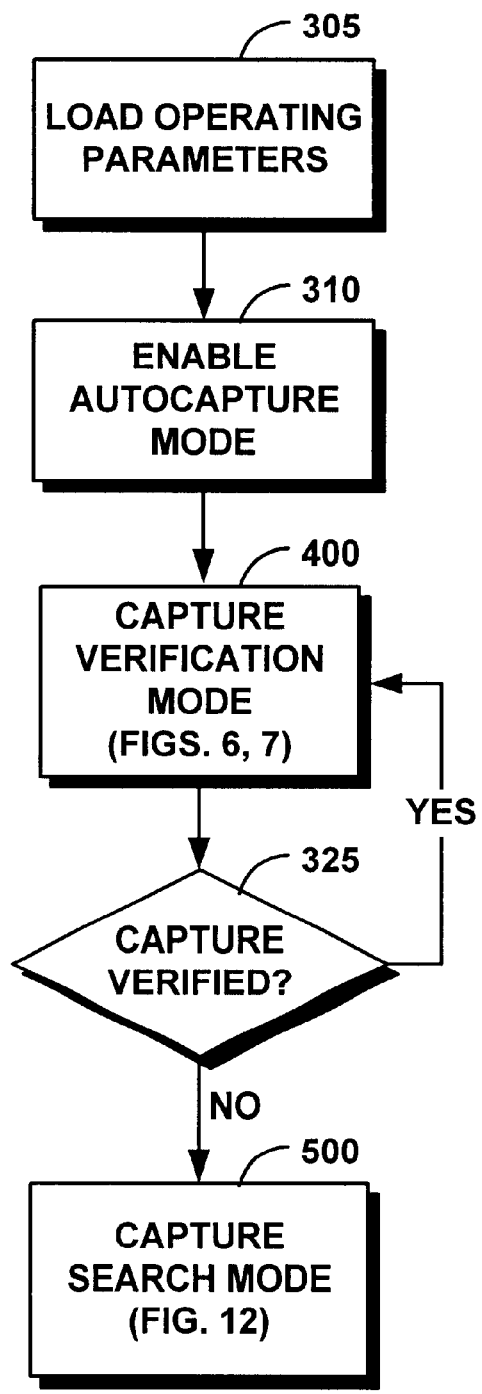
FIG. 5 is a flow chart describing an overview of the operation of one embodiment of the present invention for providing automatic capture in the implantable stimulation device of FIG. 2.

FIG. 5 illustrates a flow chart providing an overview of an automatic capture operation or method 300 as implemented in one embodiment of the stimulation device 10. In the flow chart of FIG. 5 and other flow charts described herein, the various algorithmic steps are summarized in individual "blocks". Such blocks describe specific actions or decisions that must be made or carried out as the algorithm proceeds. Where a microcontroller 60 (or equivalent) is employed, the flow charts presented herein provide the basis for a "control program" that may be used by such a microcontroller 60 to effectuate the desired control of the stimulation device 10.

The flow chart of FIG. 5 illustrates the general operating modes of the automatic capture method 300. The operating parameters necessary for the execution of various algorithms implemented by the automatic capture method 300 are loaded, at block 305, from the memory 94 into control programs residing in the microcontroller 60. The automatic capture method 300 may be enabled at block 305 via a programming command provided by a medical practitioner, at the time of implant of the stimulation device 10 or during any follow-up physician visit. The automatic capture method 300 then enters a capture verification mode at block 400. The capture verification mode or method 400 will be described in detail later in conjunction with FIGS. 6 through 11. As long as capture is verified by the capture verification mode or method 400 after delivery of a stimulation pulse 200, the automatic capture method 300 remains in the capture verification mode 400 as shown at decision step 325. If capture is not verified following the delivery of the stimulation pulse 200, the automatic capture method 300 will enter a capture search mode 500 to be described in detail later in conjunction with FIG. 12.

The capture verification method 400 will now be described in conjunction with FIG. 6, and an example illustrated in FIGS. 8 and 9. Initially, the capture verification method 400 waits for the delivery of a stimulation pulse delivery event at block 405. A stimulation pulse will typically be delivered at the end of a given escape interval. As an example, a ventricular stimulation pulse will be delivered during ventricular pacing (e.g. VVI or VVIR), if no intrinsic R-wave is detected prior to the expiration of the defined VV escape interval. During dual chamber (DDD) pacing, a ventricular stimulation pulse will be delivered at the expiration of the AV escape interval if no R-wave is detected first.

A short stimulation refractory period is initiated immediately following delivery of the stimulation pulse. The stimulation refractory period during automatic capture is preferably programmable with an exemplary nominal value of approximately 32 msec. This short refractory period prevents detection of large transient signals that occur immediately following the delivery of the stimulation pulse.

Following a stimulation pulse, a stimulation refractory and fast recharge interval is initiated at step 410. The fast recharge interval allows charge balancing to occur quickly through the heart tissue. The fast recharge interval is also preferably programmable, and, during automatic capture, it is programmed to an exemplary nominal value of approximately 15 msec.

Immediately upon request of the stimulation pulse, FRC, OPEN and BLOCK periods are triggered at step 410. The FRC, OPEN, and BLOCK periods start at the beginning of the stimulation pulse, with the OPEN period extending beyond he FRC period, and the BLOCK period extending beyond the OPEN period.

The OPEN period is set by switching circuitry within the automatic sensitivity control (ASC) hardware of the sensing circuitry 82 or 84. In an exemplary embodiment, the OPEN period is preferably set to approximately 1 msec longer than FRC when the automatic capture method 300 is enabled. The BLOCK period is also set by switching circuitry within the automatic sensitivity control (ASC) hardware. In this exemplary embodiment, the BLOCK period is set to approximately 10 msec longer than OPEN when the automatic capture method 300 is enabled.

As described in conjunction with FIG. 3, the OPEN and BLOCK periods allow ventricular sensing circuitry 84 or atrial sensing circuitry 82 to be isolated and connected to a reference potential, to prevent the respective sense amplifiers from becoming saturated by the large transient signal generated by the stimulation potential. However, when the automatic capture method 300 is enabled, the OPEN and BLOCK periods are shortened such that these events still fall within the short stimulation refractory period.

A system interrupt signal is generated at block 420 when the short stimulation refractory period expires. At block 425, an ALERT interval is initiated. During this ALERT interval, the automatic sensitivity control (ASC) hardware sets a constant value for the sense threshold, or in an alternative embodiment, the initial value of a decaying sense threshold. The duration of the ALERT interval is preferably a programmable value, and is set to an approximate value of 32 msec.

In the alternate embodiment, the sense threshold may decay over the period of the ALERT interval as controlled by the automatic sensitivity control (ASC) hardware, and an evoked response detection inquiry is initiated at decision step 435. If the sensed signal received by the atrial sensing circuitry 82 or the ventricular sensing circuitry 84 exceeds the decaying sense threshold during the ALERT interval, an evoked response detection is confirmed.

However, if the sensed signal does not exceed the decaying sense threshold during the ALERT interval, loss of capture is confirmed and method 400 inquires at block 437 if the alert time has expired. If the alert time has expired, method 400 proceeds to block 455 (FIG. 7); otherwise, method 400 returns to decision block 435.

If capture is confirmed, the method 400 proceeds to block 440 and generates a system interrupt signal to notify other system operations that capture has been achieved. This system interrupt signal notifies the microprocessor 60 to inhibit the delivery of a back-up stimulation pulse at block 442. The system interrupt signal also triggers a post-sense refractory period at block 444. The post-sense refractory period is to prevent detection of the T-wave that follows the evoked QRS complex, as T-wave sensing can cause erroneous tachycardia detection and should preferably be avoided. The post-sense refractory period is preferably a programmable value, which is set for example, to approximately 128 msec.

At the end of the post-sense refractory period, another interrupt signal is generated at step 446 to signal other system operations of the stimulation device 10 that the post-sense refractory period has expired. This interrupt signal triggers the automatic sensitivity control (ASC) hardware to reset the sense threshold at a high value and to control its decay during the remainder of the current escape interval at block 448. If an arrhythmia is detected during this time as determined at decision step 449, stimulation is terminated at step 450, and the stimulation device 10 will initiate appropriate cardioversion or defibrillation therapies. Otherwise, the method 400 returns to step 405 and awaits the delivery of the next stimulation pulse upon expiration of an escape interval.

Figure 8:
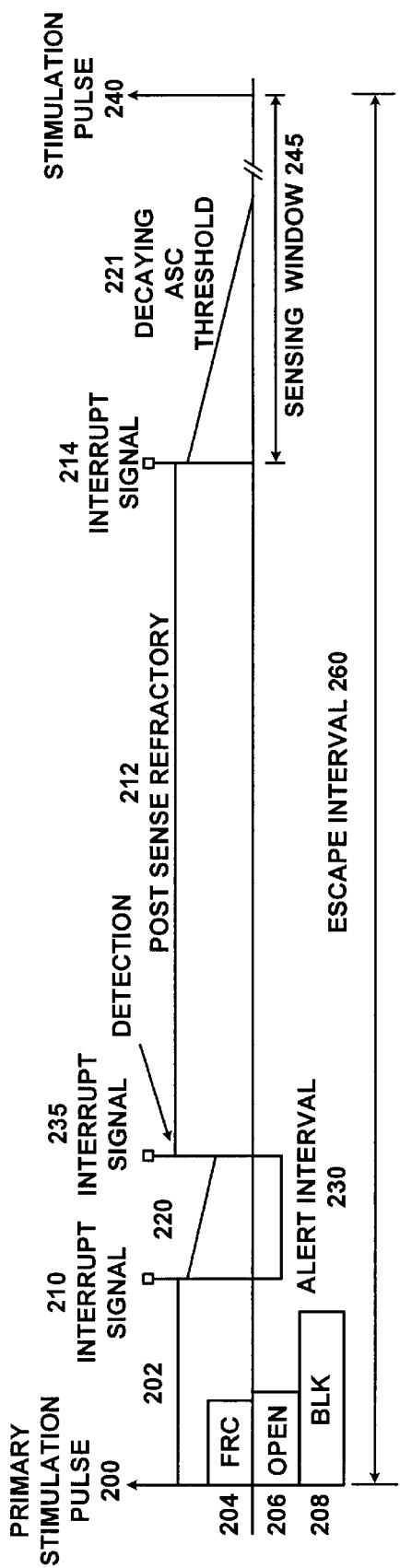
FIG. 8 is a timing diagram illustrating a sequence of events that occur during one escape interval when the automatic capture feature of the present invention is enabled and operating in the capture verification mode of FIG. 5.
Figure 9:
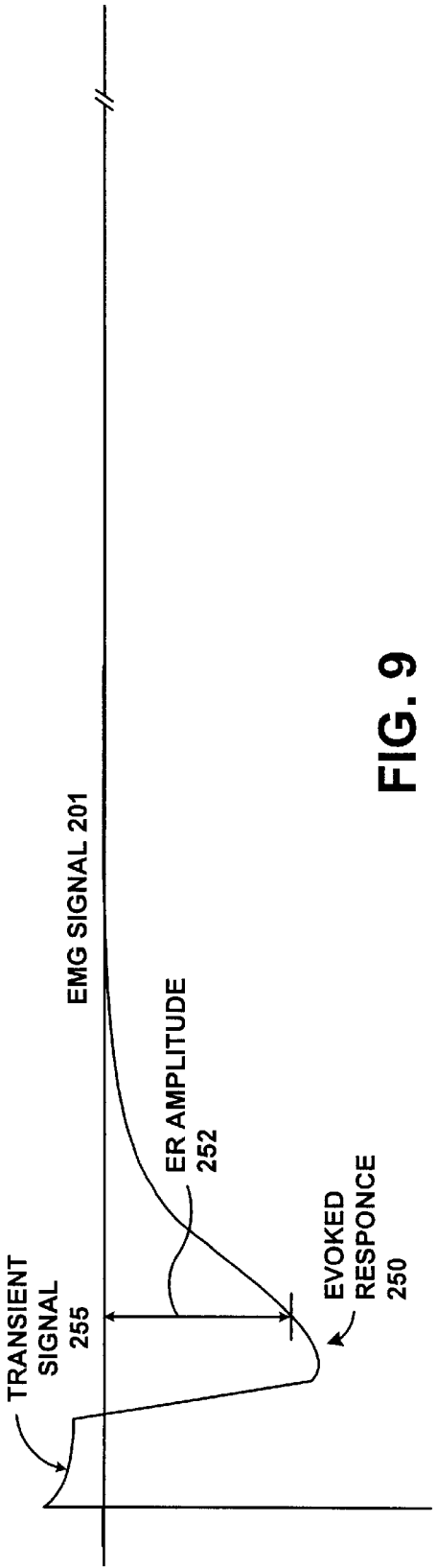
FIG. 9 is a trace representing an EGM signal corresponding to the timing diagram of FIG. 8.

These events are also illustrated by the exemplary diagram of FIGS. 8 and 9. A short stimulation refractory period 202 that is 32 msec in duration immediately follows a primary stimulation pulse 200. During this short stimulation refractory period, a fast recharge interval 204, an OPEN period 206, and a BLOCK period 208 overlap. The transient signal 255 that occurs subsequently to the primary stimulation pulse 200 is not sensed during this short stimulation refractory period 202, and the sensing circuitry is protected by the OPEN period 206 and the BLOCK 208 period. At the termination of the stimulation refractory period 202, an interrupt signal 210 is generated to notify the stimulation device 10 that the stimulation refractory period 202 has expired.

Next, the ALERT interval 230 is initiated with a fixed or decaying sense threshold 220 controlled by the automatic sensitivity control (ASC) hardware. When the amplitude 252 of the evoked response 250 exceeds the sense threshold 220, capture detection is made and a system interrupt signal 235 is generated to indicate this event. This interrupt signal 235 triggers a post-sense refractory period 212, shown to be approximately 128 msec in duration. The post-sense refractory period 212 prevents over-sensing of T-waves.

Another interrupt signal 214 is generated at the end of the post-sense refractory 212 to indicate this event to the stimulation device 10 and to trigger the decaying sense threshold 221 controlled by the automatic sensitivity control (ASC) hardware for the remainder of the escape interval 260. This entire sequence of events represents one escape interval 260, for example one VV, VVR, VA, AV, AVR, or VAR interval. A new stimulation pulse 240 will be delivered at the end of the escape interval 260 at the same pulse energy as the stimulation pulse 200, as long as an intrinsic response is not detected during a sensing window 245 prior to the expiration of the escape interval 260.

Figure 6:
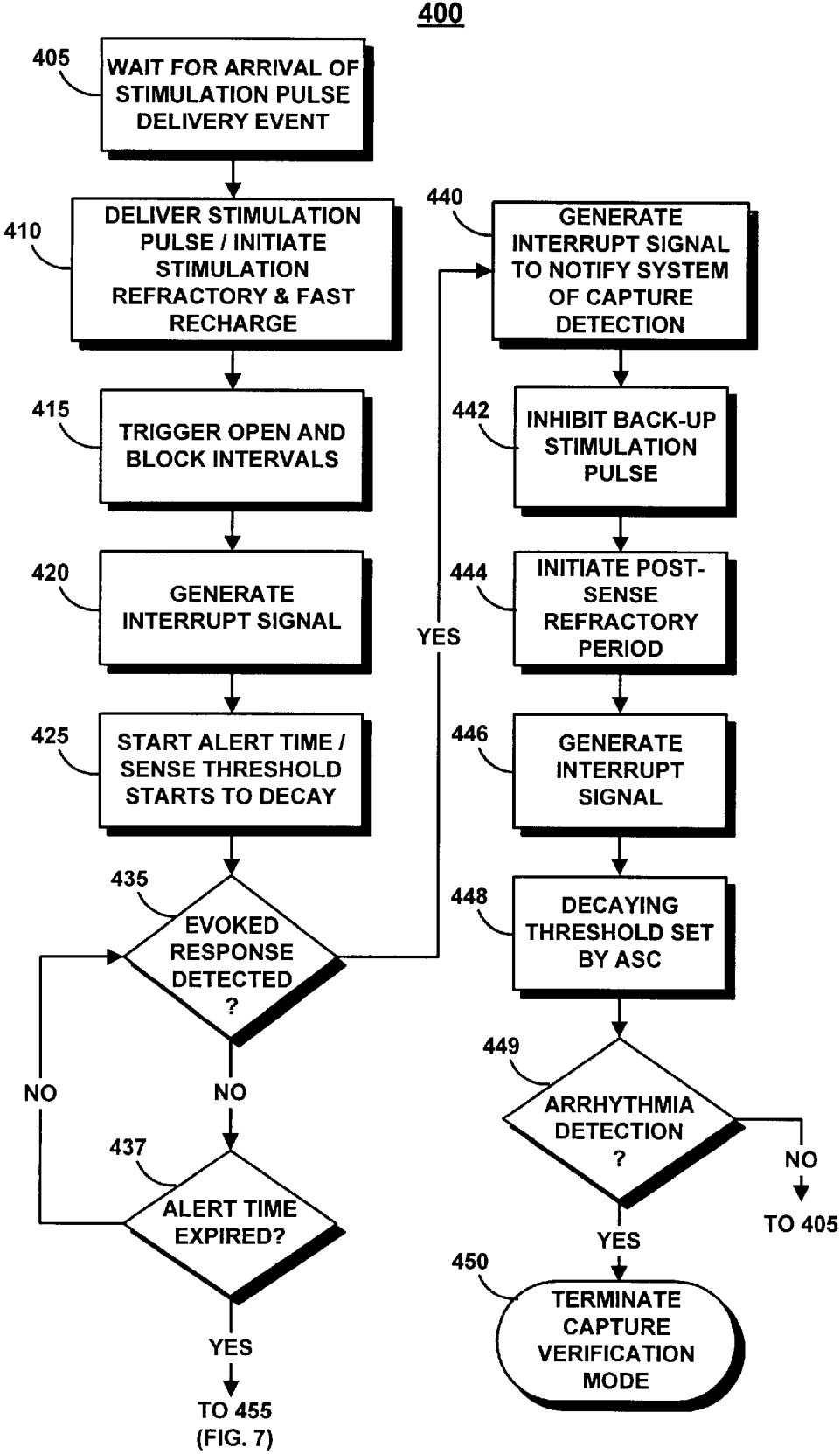
Figure 7:
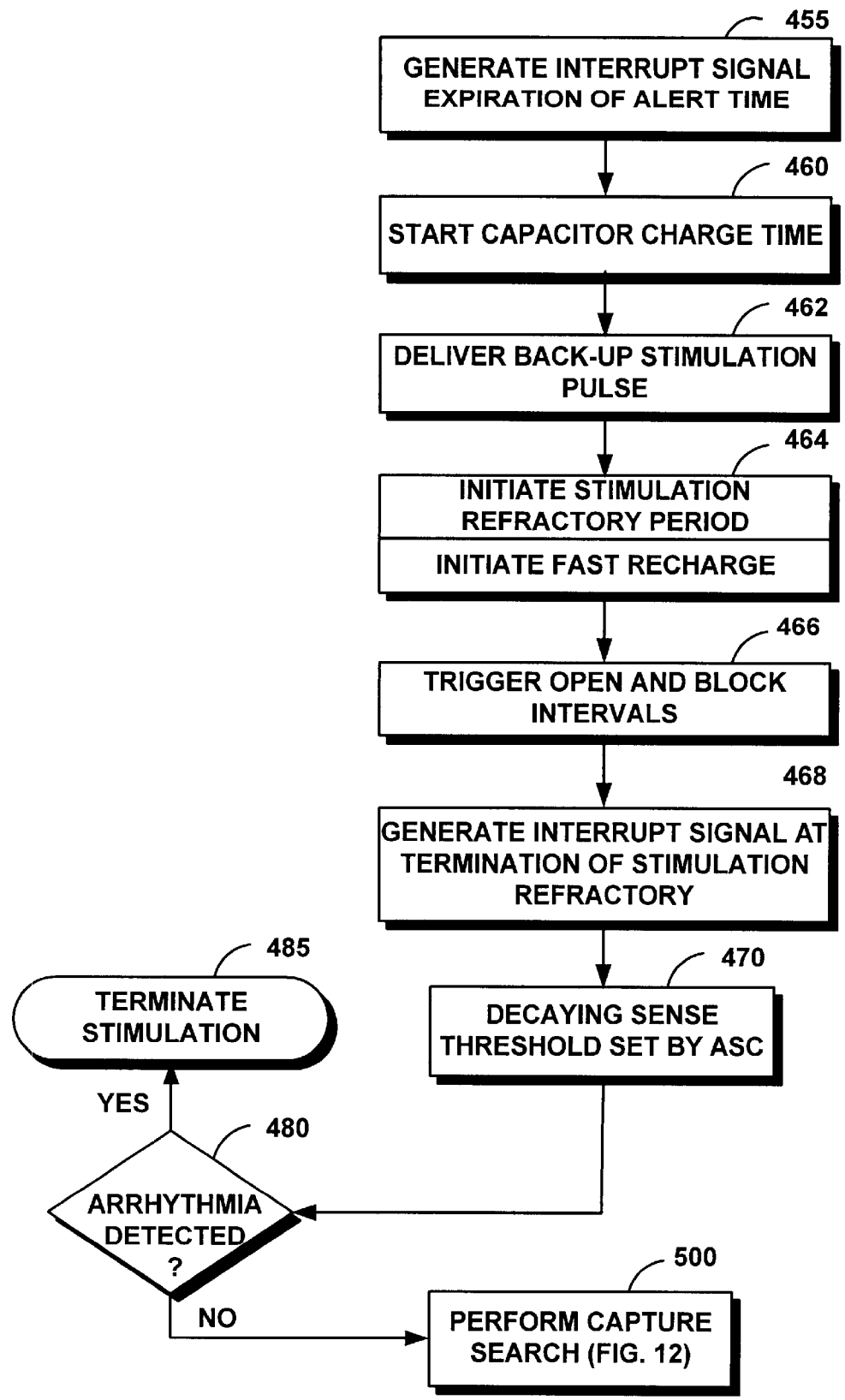
Figure 10:
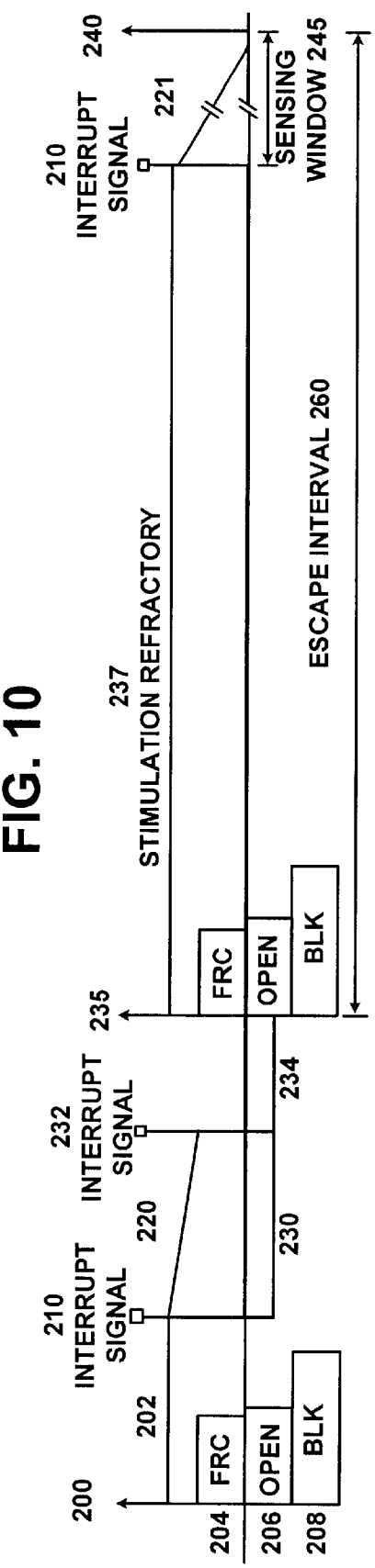
FIG. 10 is a timing diagram illustrating another sequence of events during one escape interval when the automatic capture feature of the present invention is enabled and operating in the capture verification mode of FIG. 5.
Figure 11:
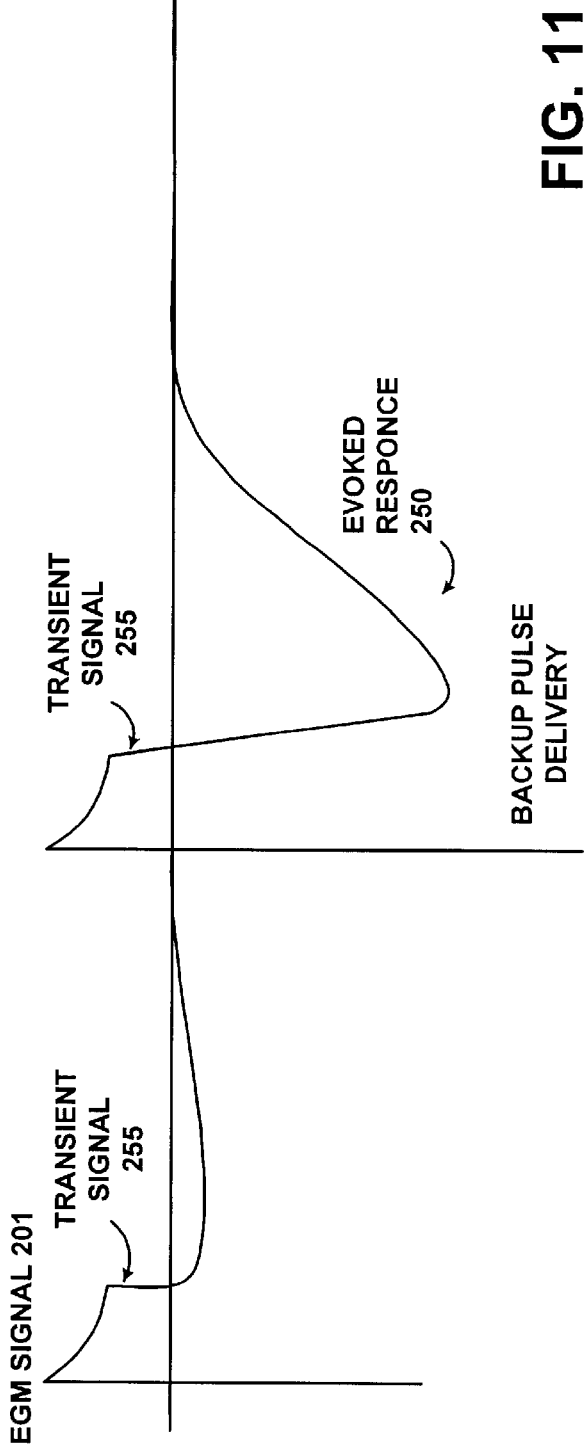
FIG. 11 is a trace representing an EGM signal corresponding to the timing diagram of FIG. 10.
Figure 12:
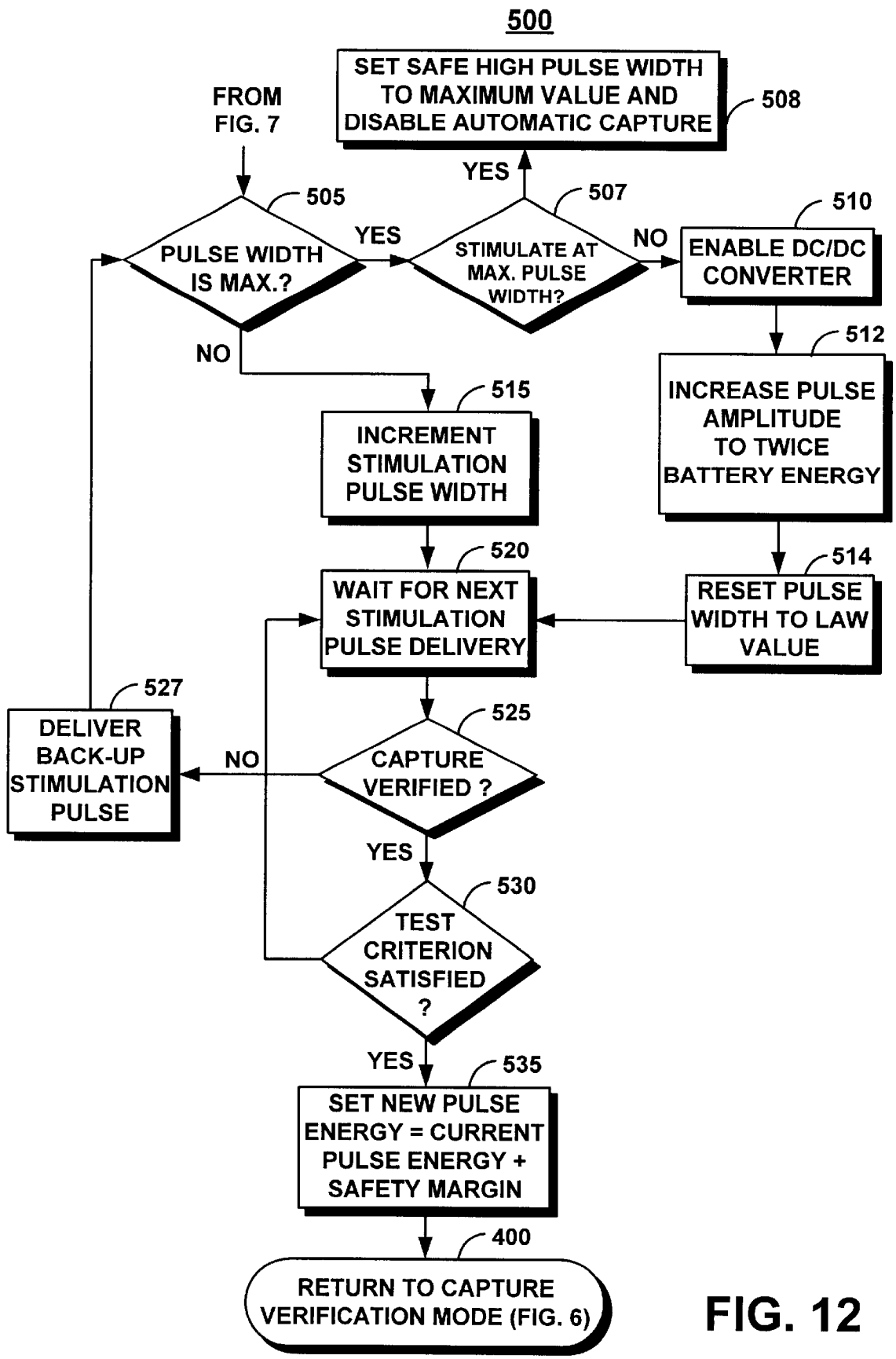
FIG. 12 is a flow chart describing an overview of one embodiment of a capture search mode included in the automatic capture feature of FIG. 5.

Referring back to FIG. 6, if no evoked response is detected at decision step 435, the method 400 proceeds to block 455 of FIG. 7, with an exemplary timing diagram illustrated in FIGS. 10 and 11. At step 455, an interrupt signal is generated to notify the stimulation device 10 that the ALERT interval for detecting an evoked response has expired. This interrupt signal indicates that a capture failure has occurred and a capacitor charge time is initiated at step 460. The capacitor charge time is preferably 20 msec and allows an output capacitor (not shown) in either the atrial pulse generator 70 or the ventricular pulse generator 72 to charge to a voltage of, for example, 1.5 to 2 times the programmed stimulation amplitude. A back-up stimulation pulse at the capacitor charge voltage (e.g. 1.5 to 2 times the programmed stimulation amplitude) is then delivered at step 462. Immediately thereafter, a stimulation refractory period and a fast recharge interval are initiated concurrently at step 464.

The fast recharge interval is immediately followed by the OPEN and BLOCK periods at step 466 which may be of the same or longer duration as during the refractory period following the primary stimulation pulse, or of different duration. Preferably, the periods are kept at the same duration in order to minimize the microprocessor 60 requirements. In the present example, the fast recharge interval is approximately 15 msec, the OPEN period is approximately 1 msec longer, and the BLOCK period is approximately 10 msec longer, totaling approximately 26 msec. However, if cross-talk were detected, these periods could be longer.

At the end of the stimulation refractory period, an interrupt signal is generated at block 468 to notify the stimulation device 10 of this event. This interrupt signal triggers the automatic sensitivity control (ASC) hardware to reset the sense threshold to a high value. The sense threshold then decays as controlled by automatic sensitivity control (ASC) hardware, at block 470, until the current escape interval expires or until an intrinsic response or tachycardia or fibrillation is detected at decision step 480.

If no arrhythmia is detected at decision step 480, the capture verification method 400 calls upon the capture search method 500 to initiate a search for the minimum stimulation energy required to achieve capture on the next stimulation cycle. It should be clear that in one embodiment, more than one capture loss is determined at decision step 480, prior to invoking the capture search method 500.

If an arrhythmia is detected at decision step 480, stimulation is terminated at step 485 so that stimulation device 10 can call upon appropriate system operations to verify arrhythmia detection and deliver cardioversion or defibrillation therapy as necessary.

The timing diagram of FIG. 10 illustrates a sequence of events that may occur during the capture verification mode 400 when no evoked response is detected as just described in conjunction with FIG. 7. The primary stimulation pulse 200 is shown followed by the short stimulation refractory period 202 within which the fast recharge interval 204, the OPEN period 206 and the BLOCK period 208 all occur, minimizing lead polarization effects and preventing detection of the large transient signal 255 associated with the stimulation pulse 200.

At the end of the stimulation refractory period 202, the interrupt signal 210 is generated triggering an ALERT interval 230 during which the automatic sensitivity control (ASC) hardware sets a fixed or decaying sense threshold 220. The ALERT interval 220 expires after the programmed 32 msec period without detecting an evoked response. An interrupt signal 232 triggers a hardware set-up for charging an output capacitor during the 20 msec delay period 234.

At the end of the capacitor charging delay period 234, a high-energy back-up stimulation pulse 235 is delivered. The back-up stimulation pulse 235 is followed by a longer stimulation refractory period 237 during which the same or longer intervals for fast recharge 204, OPEN 206 and BLOCK 208 are applied to minimize lead polarization and to avoid sensing of the transient signal 255. The longer stimulation refractory period 237 also prevents T-wave detection following the evoked response 250. No attempt is made to detect the evoked response 250 since the stimulation pulse 235 is set to a high level that should ensure capture.

At the end of the stimulation refractory period 237, an interrupt signal 210 is generated and the automatic sensitivity control (ASC) hardware resets the decaying sense threshold 221 to allow sensing for intrinsic responses during the remainder of the escape interval 260. In this case, the escape interval 260 is reset upon delivery of the back-up stimulation pulse 235 since this marks the occurrence of chamber contraction. The next primary stimulation pulse 240 will be delivered at a higher energy level than stimulation pulse 200 in accordance with the methods of the capture search mode to be described now in detail in conjunction with FIG. 12.

The capture search mode 500 (FIG. 12) begins at decision step 505 by determining if the current stimulation pulse width is at the maximum setting allowed by the stimulation device 10. If it is not, the stimulation pulse energy is increased by incrementing the pulse width by one programmable setting, typically about 61 microseconds. The method 500 then waits at step 520 for the next stimulation pulse to be delivered.

At decision step 525, capture verification is performed in the same way as described for the capture verification mode 400 (FIGS. 6, 7). That is, immediately following the stimulation pulse, a short stimulation refractory period is followed by an ALERT interval in which the evoked response can be detected. If no evoked response is detected, a back-up stimulation pulse, preferably equal to 1.5 to 2 times the current pulse amplitude, is delivered at step 527, and the method 500 returns to step 505 to verify that the pulse width has not reached a maximum, and then continues to increase the pulse energy by incrementing the pulse width (step 515).

This process continues until the capture search criterion at decision step 530 is met. Preferably, the capture search criterion requires that a specified number of consecutive capture detections, preferably two, occurs at a given pulse energy in order for the capture search to be successful. Once the capture search criterion is met at step 530, the programmed stimulation pulse energy is reset to the current pulse energy plus some safety margin. In this example, the stimulation pulse energy is adjusted by resetting the stimulation pulse width to the current pulse width plus one additional pulse width setting as a safety margin.

If, during the capture search method 500, the pulse width reaches a maximum value as determined at decision step 505 before the capture search criterion is met at step 530, then method 500 inquires at decision step 507 if it would be desirable to stimulate at this maximum pulse width. If such stimulation is desirable, method 500 sets the high pulse width to the maximum value and concurrently disables the automatic capture feature at block 508.

Returning to decision block 507, if method 500 determines that it would not be desirable to stimulate at this maximum pulse width, method 500 proceeds to enable the DC/DC converter 120 (FIG. 2) at step 510 so that the stimulation pulse amplitude can be set to, for example, twice the battery voltage at step 512. After doubling the pulse amplitude, the stimulation pulse width is reset to a relatively low value at step 514, typically the minimum pulse width available, on the order of 61 microseconds. At step 520, the method 500 waits for the next stimulation pulse to be delivered at this new amplitude and pulse width setting to determine if capture is achieved.

Once the criterion of decision step 530 is met, the pulse energy is adjusted to a setting equal to the current pulse energy plus a safety margin at step 535. In this example, adjustment is made by resetting both the programmed pulse amplitude setting to the current value and the programmed pulse width to the current value plus one additional pulse width interval as a safety margin.

If at step 535, the current pulse width is at the maximum value allowed by the stimulation device 10 such that the safety margin would cause the adjusted pulse width to exceed the allowable value, then the pulse amplitude is doubled and the capture search mode rechecks the minimum pulse width at which the capture search criteria is met. The capture search mode 500 is thus completed and returns to the capture verification mode 400 and remains there until a capture failure is detected or the automatic capture feature (or method 300) is disabled.

While one algorithm for adjusting pulse energy during a capture search mode 500 has been described, other algorithms for searching for sustained capture may be used in conjunction with the present invention.

Figure 13:
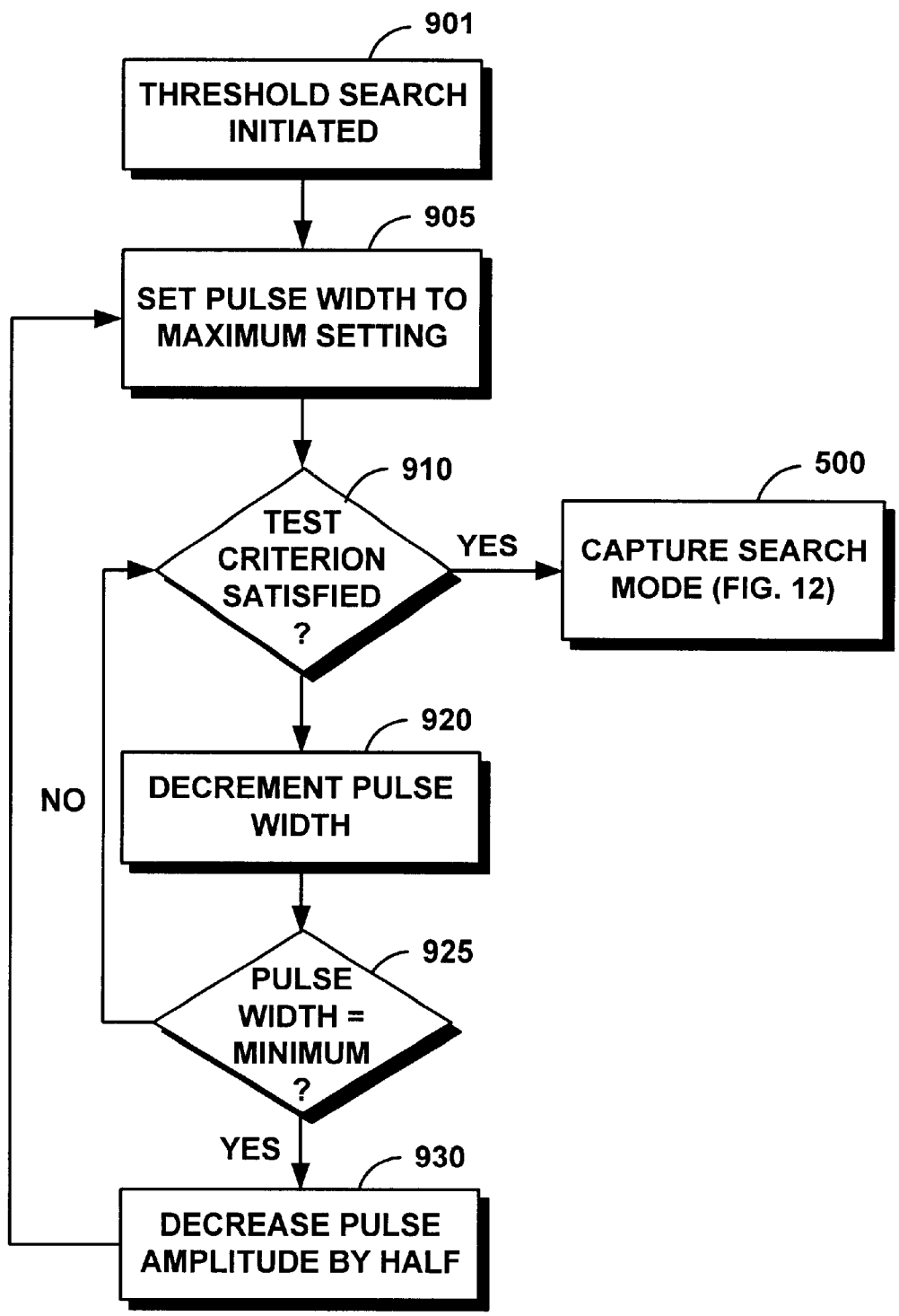
FIG. 13 is a flow chart describing an overview of one embodiment of a threshold search mode included in the automatic capture feature of FIG. 5.

Yet another mode of operation of the present invention, namely automatic threshold test mode or method 900, is illustrated in the flow chart of FIG. 13. Automatic threshold testing may be performed upon a programmed command or periodically, such as daily, weekly or monthly, or upon an event-related trigger from microprocessor 60. Upon receiving a trigger initiating the automatic threshold test at step 901, the microprocessor 60 (FIG. 2) sets the stimulation pulse width to a high setting at step 905. This setting may be the maximum pulse width setting available or it may be some multiple, for example twice, the currently programmed pulse width setting. According to a preferred embodiment, the pulse width could remain at the same setting at which capture was last verified.

The threshold test mode 900 then progressively decreases the stimulation pulse energy until a threshold test criterion is satisfied at decision step 910. For example, a specified number of cycles in which the current pulse energy fails to capture the paced chamber, preferably two consecutive capture failures. Initially, the pulse width setting is adjusted to a level that is expected to capture the paced chamber, therefore the criterion at decision step 910 is not met and the pulse width will be decremented at step 920.

At decision step 925, the method 900 determines if the pulse width has reached the minimum setting available to the stimulation device 10. If not, the method 900 returns to decision step 910 to determine if two consecutive capture failures occur at the reduced pulse energy. If the pulse width is already at a minimum setting at step 925, then the pulse amplitude will be decreased by half at step 930 and the pulse width will be reset to a relatively high value at step 905.

This process continues until the threshold search criterion at step 910 is met. Once the threshold search criterion is met, the threshold test mode 900 calls upon capture search mode 500 (FIG. 12) to make the final adjustments to the programmed pulse amplitude and pulse width after identifying the settings at which the capture search criterion is met.

While one algorithm has been described in detail for adjusting pulse energy until threshold is found, other algorithms for performing a threshold search could also be used in conjunction with the present invention.

Thus, a method for performing beat-by-beat automatic capture is provided in a combination cardiac stimulating device that provides bradycardia, tachycardia and fibrillation therapies without compromising accurate tachycardia and fibrillation detection or other data collection and diagnostic capabilities and without additional hardware or circuitry requirements. Verifying capture and providing a back-up stimulation pulse when capture is lost ensures effective stimulation therapy delivery, thereby improving overall device performance. By automatically adjusting the stimulation energy whenever capture is lost, battery longevity is improved.

It is to be understood that the specific embodiments of the invention that have been described are merely illustrative of certain application of the principle of the present invention. Numerous modifications may be made without departing from the spirit and scope of the present invention.

What is claimed is:

1. A cardiac stimulation method, comprising:
   sensing for intrinsic cardiac activity within a cardiac chamber during an escape interval;
   if no intrinsic cardiac activity is sensed within the escape interval, delivering a stimulation pulse for stimulating the cardiac chamber;
   initiating a stimulation refractory period following the delivery of the stimulation pulse to prevent sensing of events associated with an evoked response, wherein initiating the stimulation refractory period includes starting three events: a fast recharge period, an OPEN interval, and a BLOCK interval; and
   upon expiration of the stimulation refractory period, generating an interrupt signal to indicate that the stimulation refractory period has expired, setting a sensing threshold to a high level, and causing the sensing threshold to decay to a low level.

2. The cardiac stimulation method according to claim 1, wherein upon the expiration of the stimulation refractory period, further setting a sensing window for sensing intrinsic cardiac activity.

3. The cardiac stimulation method according to claim 2, wherein if no intrinsic cardiac activity is sensed during the sensing window, delivering another stimulation pulse at the expiration of the sensing window.

4. The cardiac stimulation method according to claim 3, wherein causing the sensing threshold to decay includes detecting low amplitude signals.

5. The cardiac stimulation method according to claim 4, wherein detecting low amplitude signals includes detecting signals associated with fibrillation.

6. The cardiac stimulation method according to claim 3, wherein initiating the stimulation refractory period to prevent sensing of events associated with the evoked response includes preventing the sensing of T-waves.

7. The cardiac stimulation method according to claim 3, wherein setting the sensing threshold to a high level includes allowing the detection of high amplitude cardiac signals.

8. The cardiac stimulation method according to claim 7, wherein allowing the detection of high amplitude cardiac signals includes allowing the detection of any one or more of: an R-wave or a P-wave.

9. The cardiac stimulation method according to claim 3, wherein causing the sensing threshold to decay to a low level includes causing the sensing threshold to decay at a predetermined rate.

10. The cardiac stimulation method according to claim 9, wherein causing the sensing threshold to decay at a predetermined rate includes causing the sensing threshold to decay at a programmable rate.

11. The cardiac stimulation method according to claim 1, wherein initiating the stimulation refractory period includes setting a programmable duration for the stimulation refractory period.

12. The cardiac stimulation method according to claim 11, wherein setting the duration for the stimulation refractory period includes setting the duration to approximately 256 msec.

13. The cardiac stimulation method according to claim 1, wherein setting the fast recharge period includes:
   initiating the fast recharge period immediately following the stimulation pulse;
   extending the OPEN interval beyond the fast recharge interval; and
   extending the BLOCK interval beyond the OPEN interval.

14. The cardiac stimulation method according to claim 3, further including a method for automatically verifying capture and, as necessary, automatically delivering a back-up stimulation pulse when capture is lost.

15. The cardiac stimulation method according to claim 14, further including adjusting the energy of the stimulation pulse to a level safely above a minimum capture energy, subsequent to delivering the back-up stimulation pulse.

16. The cardiac stimulation method according to claim 14, further including a method for maintaining capture by using a capture search technique.

17. The cardiac stimulation method according to claim 16, wherein using a capture search technique includes, when loss of capture is detected, re-determining the minimum capture energy, delivering a series of test stimulation pulses at progressively increasing energy levels, using the method for automatically verifying capture to detect when capture is achieved.

18. The cardiac stimulation method according to claim 16, further including an automatic threshold testing method that determines the minimum capture energy.

19. A method of performing automatic capture in a cardiac stimulation device, comprising:
   sensing for intrinsic cardiac activity within a cardiac chamber during an escape interval;
   if intrinsic cardiac activity is not sensed within the escape interval, delivering a stimulation pulse for stimulating the cardiac chamber; and
   upon expiration of a stimulation refractory period, generating an interrupt signal to indicate that the stimulation refractory period has expired, setting a sensing threshold to a high level, causing the sensing threshold to decay to a low level during an alert interval, and verifying capture during the alert interval.

20. The method according to claim 19, wherein verifying capture includes verifying that the stimulation pulse produced an evoked response during the alert interval.

21. The method according to claim 20, wherein if no evoked response is sensed during the alert interval, delivering a back-up stimulation pulse; performing a capture search for determining a minimum capture energy needed to reliably achieve capture; and adjusting the energy of the stimulation pulse to a level safely above the minimum capture energy.

22. The method according to claim 20, wherein delivering the stimulation pulse includes initiating two simultaneous events: the stimulation refractory period is initiated immediately following the delivery of the stimulation pulse to prevent detection of large transient signals that occur immediately following the delivery of the stimulation pulse; and a fast recharge interval that allows fast charge balancing to occur.

23. The method according to claim 22, wherein initiating the stimulation refractory period includes initiating a refractory period of approximately 32 msec; and
   wherein initiating the fast recharge interval includes initiating a fast recharge interval of approximately 15 msec.

24. The method according to claim 19, further including initiating the alert interval immediately following the stimulation refractory period.

25. The method according to claim 19, wherein if a sensed evoked response exceeds the sensing threshold during the alert interval, confirming capture; and
   if the sensed evoked response does not exceed the sensing threshold during the alert interval confirming loss of capture.

26. The method according to claim 25, wherein if capture is confirmed:
   generating an interrupt signal to inhibit delivery of a back-up stimulation pulse; and
   triggering a post-sense refractory period to prevent detection of a signal that follows an evoked response.

27. The method according to claim 26, wherein triggering the post-sense refractory period includes initiating a period of approximately 128 msec.

28. The method according to claim 26, wherein if capture is confirmed:
   generating another interrupt signal at the end of the post-sense refractory period to reset the sensing threshold to the high level;
   setting a sensing window following said another interrupt signal for sensing intrinsic cardiac activity; and
   causing the sensing threshold to decay during the sensing window.

29. The method according to claim 28, wherein if loss of capture is confirmed generating an interrupt signal at the termination of the alert interval, and initiating a delay interval.

30. The method according to claim 29, further including, at the expiration of the delay interval:
   delivering a back-up stimulation pulse; and
   initiating an extended stimulation refractory period followed by a sensing window.

31. The method according to claim 30, further including at the end of the extended stimulation period:
   generating another interrupt signal to reset the sensing threshold to the high value;
   causing the sensing threshold to decay during the sensing window; and
   wherein if no intrinsic response is detected during the sensing window, initiating a capture search method to search for a minimum capture stimulation energy required to achieve capture in a subsequent stimulation cycle.

32. A cardiac stimulation device adapted with an automatic capture feature, comprising:
   sensing circuitry configured to detect intrinsic cardiac activity within a cardiac chamber during an escape interval;
   a pulse generator, responsive to the sensing circuitry, that delivers a stimulation pulse if no intrinsic cardiac activity is sensed within the escape interval;
   a processor, responsive to a stimulation refractory period, that receives an interrupt signal that indicates that the stimulation refractory period has expired, sets a sensing threshold to a high level evoked response threshold, causes the sensing threshold to decay to a low level during an alert interval, and verifies capture during the alert interval.

33. The cardiac stimulation device according to claim 32, wherein if no evoked response is sensed during the alert interval, the pulse generator delivers a back-up stimulation pulse; performs a capture search for determining a minimum capture energy needed to reliably achieve capture; and adjusts the energy of the stimulation pulse to a level safely above the minimum capture energy.

34. The cardiac stimulation device according to claim 33, wherein the processor further initiates the alert interval immediately following the stimulation refractory period.

35. The cardiac stimulation device according to claim 34, wherein if a sensed evoked response exceeds the sensing threshold during the alert interval, the processor confirms capture; and
   if the sensed evoked response does not exceed the sensing threshold during the alert interval, the processor confirms loss of capture.

36. The cardiac stimulation device according to claim 35, wherein if capture is confirmed:
   the processor receives an interrupt signal to inhibit delivery of a back-up stimulation pulse; and
   triggers a post-sense refractory period to prevent detection of a signal that follows an evoked response.

37. The cardiac stimulation device according to claim 36, wherein if capture is confirmed:
   the processor receives another interrupt signal at the end of the post-sense refractory period to reset the sensing threshold to the high level;
   the processor sets a sensing window following said another interrupt signal for the sensing circuitry to sense intrinsic cardiac activity; and
   the processor causes the sensing threshold to decay during the sensing window.

38. The cardiac stimulation device according to claim 37, wherein if loss of capture is confirmed:

the processor receives an interrupt signal at the termination of the alert interval, and initiates a delay interval; and at the expiration of the delay interval, the pulse generator delivers a back-up stimulation pulse, and the processor initiates an extended stimulation refractory period followed by a sensing window.

* * * * *